(12) United States Patent
Clavey

(10) Patent No.: US 9,309,177 B2
(45) Date of Patent: Apr. 12, 2016

(54) PROCESS FOR PREPARING OR RECOVERING ACETALS OR KETALS BY MEANS OF PERVAPORATION

(75) Inventor: Thomas Clavey, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/130,683

(22) PCT Filed: Jun. 29, 2012

(86) PCT No.: PCT/EP2012/062753
§ 371 (c)(1),
(2), (4) Date: Apr. 4, 2014

(87) PCT Pub. No.: WO2013/004631
PCT Pub. Date: Jan. 10, 2013

(65) Prior Publication Data
US 2014/0288333 A1    Sep. 25, 2014

(30) Foreign Application Priority Data

Jun. 7, 2011 (EP) .................................... 11172867

(51) Int. Cl.
| | |
|---|---|
| *C07C 41/56* | (2006.01) |
| *C07C 41/58* | (2006.01) |
| *B01D 61/00* | (2006.01) |
| *C07C 41/50* | (2006.01) |
| *B01D 61/36* | (2006.01) |

(52) U.S. Cl.
CPC .............. *C07C 41/50* (2013.01); *B01D 61/362* (2013.01); *C07C 41/56* (2013.01); *C07C 41/58* (2013.01); *B01D 2311/08* (2013.01); *B01D 2311/2623* (2013.01); *B01D 2317/022* (2013.01)

(58) Field of Classification Search
CPC ....... C07C 41/56; C07C 41/58; B01D 61/362
USPC ......................................................... 568/594
See application file for complete search history.

(56) References Cited

U.S. PATENT DOCUMENTS

| | | | |
|---|---|---|---|
| 6,806,392 B2 * | 10/2004 | Boesch et al. ................ | 568/594 |
| 2004/0024260 A1 | 2/2004 | Winkler et al. | |

FOREIGN PATENT DOCUMENTS

EP    1 167 333    1/2002

OTHER PUBLICATIONS

International Search Report for PCT/EP2012/062753, mailed Oct. 5, 2012.

* cited by examiner

*Primary Examiner* — Sikarl Witherspoon
(74) *Attorney, Agent, or Firm* — Nixon & Vanderhye P.C.

(57) ABSTRACT

The process of the present invention comprises reacting an aldehyde or ketone with an alcohol in the presence of a solid acid, and removing water and methanol from the reaction product by pervaporation, characterized in that a membrane having a flux density for water of 0.04 to 2.8 kg/(hm$^2$) is used to remove the water and another membrane having a flux density for methanol of 2.0 to 100 kg/(hm$^2$) is used to remove the methanol.

9 Claims, 1 Drawing Sheet

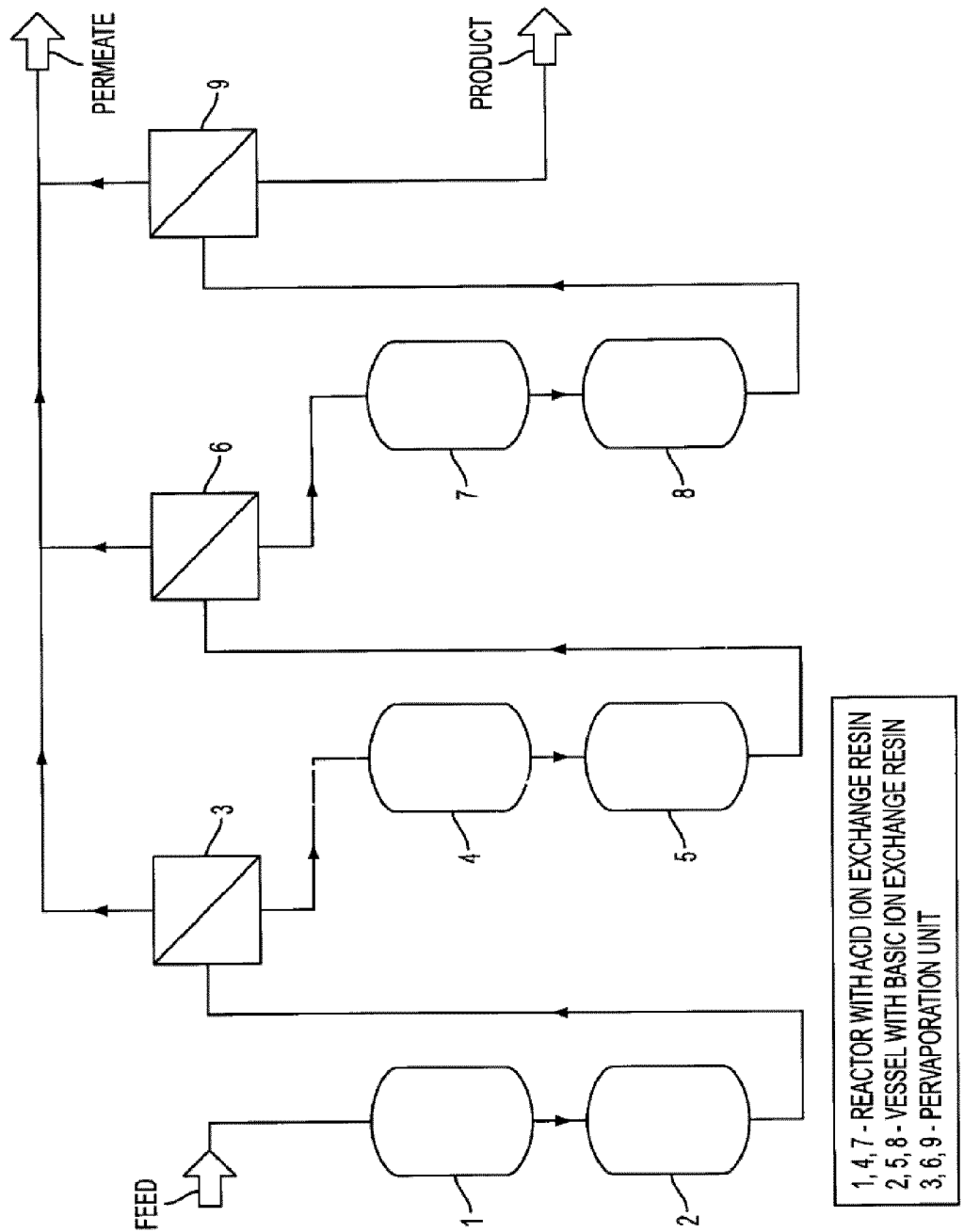

PROCESS FOR PREPARING OR RECOVERING ACETALS OR KETALS BY MEANS OF PERVAPORATION

This application is the U.S. national phase of International Application No. PCT/EP2012/062753 filed 29 Jun. 2012 which designated the U.S. and claims priority to EP Patent Application No. 11172867.1 filed 6 Jul. 2011, the entire contents of each of which are hereby incorporated by reference.

The present invention is related to an improved process for preparing acetals and ketals.

It is known that acetals and ketals can be prepared by reacting an aldehyde or ketone with an alcohol in the presence of an acidic catalyst. However, the reaction is reversible and, at ambient temperature or above, the equilibrium of the reaction is shifted to the side of the starting materials, acetal or ketone, and alcohol.

The present invention provides a process for the continuous preparation of acetals and ketals in concentrated form and avoids energy-intensive destillation procedures of conventional manufacturing processes, which are often rendered difficult by the formation of azeotropes.

Thus, the invention is concerned with a process for the preparation of acetals or ketals which comprises reacting an aldehyde or ketone with an alcohol in the presence of solid acid and removing water and methanol from the reaction product by pervaporation, characterized in that a membrane having a flux density for water of 0.04 to 2.8 kg/(hm$^2$) is used to remove the water and another membrane having a flux density for methanol of 2.0 to 100 kg/(hm$^2$) is used to remove the methanol.

More specifically, the present invention is concerned with a process for recovering acetals or ketals from reaction mixtures obtained by reacting an aldehyde or ketone with an alcohol, particularly by reaction of a lower aliphatic aldehyde or ketone with a lower aliphatic alcohol or sugar alcohol, in the presence of an acid which process comprises subjecting the reaction mixture containing an acetal or ketal together with water and unreacted aldehyde or ketone and alcohol, to treatment with a base followed by pervaporation.

The term "lower" as used herein denotes compounds having 1 to 7 carbon atoms. Examples of lower aliphatic ketones are acetone and methyl ethyl ketone. Examples of lower aliphatic aldehydes are formaldehyde, acetaldehyde, propionic aldehyde, butyric aldehyde and isobutyric aldehyde. Examples of alcohols are methanol and ethanol. Sorbose is an example of a sugar alcohol.

Pervaporation is a known method for separating liquids from mixtures thereof, e.g., for separating water from mixtures with organic liquids, such as alcohols, aldehydes or ketones, see, e.g., European Patent No. 0 096 339, and Chem. Eng. Technol. 19 (1996) 117-126. In pervaporation processes, the different ability of liquids or gases to permeate polymer membranes is used to separate mixtures thereof.

Pervaporation processes to remove water from esterification reactions are known. Pervaporation processes to remove reaction water from acetalisation or ketalisation processes are also known (U.S. Pat. No. 6,806,392). One of the main issues of pervaporation processes is that they have to be carried out at elevated temperature to work. But at such conditions the equilibrium of the acetalisation or ketalisation reaction is shifted markedly to the side of the starting materials of the reaction.

Surprisingly, it has been found out that when membranes with specific properties are used to remove the water and to remove the methanol the equilibrium of the reaction is shifted to the side of the reaction products.

According to the present invention, the flux density of the membrane used in the process to remove the water is from 0.04 to 2.8 kg/(hm$^2$). The flux density depends on the water concentration at the feed. When the water concentration is about 0.5 to 3 weight-% (wt-%), based on the total weight of mixture at the feed, then the flux density is usually between 0.04 and 1 kg/(hm$^2$); when the water concentration is about 3 to 7 wt-%, then the flux density is usually between 1 and 2.8 kg/(hm$^2$). The flux density of the second membrane used in the process to remove the methanol from the reaction mixture is from 1 to 100 kg/(hm$^2$). The flux density depends on the methanol concentration at the feed. When the methanol concentration is about 30 to 50 wt-%, based on the total weight of the mixture at the feed, then the flux density is usually between 10 and 100 kg/(hm$^2$); when the water concentration is about 2 to 30 wt-%, then the flux density is usually between 1 and 10 kg/(hm$^2$).

In a preferred embodiment, the process is carried out in a number of consecutive steps. In a first step, an alcohol is reacted with an aldehyde or ketone in the presence of a solid acid to obtain an equilibrium mixture comprising the reactants, the desired acetal or ketal, and water. In a second step, the equilibrium mixture obtained is subjected to treatment with a solid base followed by pervaporation. In a third step the pervaporation retentate is subjected to treatment with a solid acid under conditions that favour acetalisation or ketalisation. In a fourth step, the product from the third step treated with a solid base followed by pervaporation. The removal of water from the pervaporation retentate is repeated until the acetal or ketal is obtained in the desired purity which is determined by the requirements of the ultimate use of the acetal or ketal, i.e. by the requirements of the reactions wherein the acetal or ketal is processed further.

It is also preferred that methanol is added to the reaction mixture after the first and after each of the following pervaporation steps. The addition of methanol can have a positive effect on the shift of the equilibrium.

The removal of the methanol from the pervaporation retentate can be done to overcome the azeotropic boundary in order to recycle unconverted raw materials and achieve pure acetal in a concentration >95 wt.-%.

The process of this invention can be applied to any acetalisation or ketalisation reaction. Examples of such reactions are:

Conversion of acetone to 2,2-dimethoxypropane;
Conversion of methyl ethyl ketone to dimethoxybutane;
Conversion of sorbose to sorbose diacetonide;
Conversion of butendiol to isopropoxydioxepen;
Conversion of methylglyoxal to dimal.

In a more preferred aspect, the process of this invention is used to prepare 2,2-dimethoxypropane from acetone and methanol.

In the first step of the reaction in accordance with the invention the solid acid is suitably a strongly acidic polymer such as a polystyrene sulfonic acid, which may be macroporous or gel-type. Ion exchange resins conventionally used to catalyze ketalisation reactions can be used. Examples of such ion exchange resins are Dowex 50® (Dow Chemical), Amberlite IR 120®, Amberlyst A 15® and A 36® (Rohm & Haas), Lewatit® (Bayer). The reaction temperature is suitably from about −100° C. to about 30° C., preferably from about −80° C. to about 10° C.

Examples of bases as used in the second reaction step are weakly basic ion exchange resins such as polystyrenes resins carrying quaternary ammonium groups, e.g. IRA 96® (Rohm & Haas).

For the pervaporation, any membrane which is resistant to the reaction products and which are permeable for water may be used. Examples of such membranes are hydrophilic membranes which may be polymer or ceramic membranes. Polymer membranes may be composite membranes comprising a support layer, e.g. on the basis of acrylnitril polymers, and a polyvinyl alcohol layer which provides the actual active separating layer.

Examples of membranes useful in the process of this invention are membranes provided by Sulzer Chemtech GmbH, D-66540 Neunkirchen, Germany under the name Pervap 1211, Pervap 2201, Pervap 2255-70 and Pervap 2255-80; as well as membranes provided by CM-CELFA Membrantechnik AG, CH-6423 Seewen, Switzerland, under the name CMC-CE-01, CM-CE-01 and CMC-VP-31. Examples of inorganic membranes useful in the process of this invention are turbular Zeolith A membranes provided by Mitsui Engineering & Shipbuilding Co., Ltd., 3-16, Nihonbashi 1-chome, Chuo-ku, Tokyo 103-0027, Japan, under the name of NaA. Other membranes which are suitable are Zeolith X, Y and ZSM-5 membranes. Another example of a ceramic membrane is the Hybsi membrane by ECN licensed by Pervatech BV, 7468MC Enter, The Netherlands.

The pervaporation is suitably carried out at elevated temperatures, i.e., temperatures up to the boiling point of the reaction mixture on the retentate side of the membrane. In general, the pervaporation is carried out at about 60° C. to about 150° C. The pressure in the pervaporation is not critical and is basically determined by the pressure required to sustain the mass flow. However elevated pressure, e.g., up to 16 bar on the retentate side of the membrane can be used, subject to the mechanical resistance of the membrane, to increase the boiling point of the reaction mixture, thus allowing the pervaporation to proceed at higher temperature. The pressure on the permeate side of the membrane is suitably about 1 to about 500 mbar.

The invention is further illustrated by FIG. 1 which provides a mass flow scheme for obtaining substantially pure 2,2-dimethoxy propane from acetone and methanol, but which may find use for other ketals according to the invention.

According to the process in FIG. 1, a mixture of acetone and methanol in a molar ratio of about 2 to about 6 moles, preferably about 4 moles of methanol to one mole of acetone is cooled and fed into reactor 1 which contains an acid ion exchange resin. Reactor 1 is cooled to an appropriate temperature favouring ketal formation, e.g., to a temperature of from about −80° C. to about −45° C. The flow of the reaction mixture is regulated to allow the reaction mixture to achieve the state of the equilibrium.

Depending on the dimension of the reactor the mean residence time of the reaction mixture may vary between 1 and 10 minutes. The reaction product exiting reactor 1 and containing the desired product, 2,2-dimethoxy propane, in admixture with water, acetone and methanol is then fed through vessel 2 which contains a basic ion exchange resin into a pervaporation unit 3. Suitably, a heat exchange device and a heater is provided between 2 and 3 (not shown in FIG. 1) to allow heat transfer from the acetone/methanol mixture to reaction product exiting 2 and to adjust the temperature required for the pervaporation (about 60 to 130° C.). The permeate from the pervaporation unit 3 consists of methanol, water, minor amounts of acetone and traces of ketal.

Retentate from the pervaporation unit 3 containing ketal, acetone, methanol and water that was not fully removed in pervaporation unit 3 is cooled to a temperature of from about −80° C. to about −45° C. and fed into reactor 4 where it is allowed to achieve the state of equilibrium. The reaction mixture then proceeds via basic ion exchange resin bed 5, suitably passing a heat exchange device as in the first reaction step, to pervaporation unit 6. The process of adjusting the equilibrium of the retentate at low temperature and submitting the product again to pervaporation may be repeated as shown (7, 8, 9). While FIG. 1 shows three reaction steps it is to be understood that the process of this invention is not so limited. Depending on the reaction components involved and the requirements concerning the purity of the desired ketal, one or more reaction steps may be appropriate. In the preparation of 2,2-dimethoxy propane, 3 or 4 reaction steps suffice to obtain a product of the desired purity as required for the further use of the product.

As will be apparent from the above, the ketalisation reaction is carried out at low temperature whereas the pervaporation is carried out at elevated temperature. Therefore, in a further aspect of the invention, the heat obtained in cooling the reactants in the ketalisation reaction is used to heat up the equilibrium mixture containing the ketal prior to pervaporation. The following Example further illustrates the process of this invention.

EXAMPLE

A mixture consisting of 70 wt-%, based on total weight of the mixture at the feed, of methanol (factory regenerate; corresponding to ca. 63 wt-% of pure methanol in total) and 30 wt-% of acetone was fed into reactor 1 of an equipment corresponding to the one shown in FIG. 1 but consisting of four units (one unit=reactor with acid ion exchange resin, vessel with basic ion exchange resin, and pervaporation unit) with a flow rate of 1.0 kg per hour. The reactors with acid ion exchange resin had a volume of a volume of ca. 0.7 l and were charged with 530 g of AMBERLYST A 15®. The vessels with basic exchange resin had a volume of 0.17 l and were charged with 120 g of AMBERLITE IRA 96®.

The reactors and the connecting tubes were made of glass except the pervaporation unit and the tubes leading from the pervaporation unit to the permeate side. The temperature in the reactors charged with acid ion exchange resin was adjusted to maintain an exit temperature of −45° C. to −50° C. In the pervaporation units the membrane surface was 0.1 m$^2$; the temperature was adjusted to 95° C.; the pressure at the side of the retentate (i.e., before the membrane) was 4 bar (abs.), the pressure at the side of the permeate (i.e., behind the membrane) was 13 to 38 mbar. Membranes of the type Pervap® 1211 and Pervap® 2255-80 were used. The results obtained are given in the Table below:

| Reaction Step | Outlet reactor 1 | Outlet reactor 2 | Outlet reactor 3 | Outlet of system |
|---|---|---|---|---|
| water content | 4.6% | 1.2% | 0.7% | 0.1% |
| ketal content | 31.8% | 39.1% | 45.5% | 54.8% |
| retentate/feed ratio | 86.1% | 93.2% | 78.5% | — |

The invention claimed is:

1. A process for the preparation of acetals or ketals which comprises:
   (i) reacting an aldehyde or ketone with an alcohol in the presence of a solid acid at a reaction temperature of between about −80° C. to about −45° C. to form a reaction product mixture, and
   (ii) removing water and methanol from the reaction product mixture by pervaporation, wherein step (ii) includes removing the water from the reaction product mixture by bringing the reaction product mixture into contact with a first membrane having a flux density for water of 0.04 to 2.8 kg/(hm$^2$), and removing the methanol from the reaction product mixture by bringing the reaction product mixture into contact with a second membrane having a flux density for methanol of 2.0 to 100 kg/(hm$^2$), and wherein step (ii) is practiced under a temperature condition of about 60° C. to about 150° C. and under pressure conditions of a pressure on a retentate side of the membrane of up to 16 bar and a pressure on a permeate side of the membrane of about 1 to 500 mbar.

2. A process for recovering acetals or ketals from a reaction product mixture obtained by reacting aldehydes or ketones with alcohols at a reaction temperature of between about −80° C. to about −45° C. in the presence of a solid acid, wherein the process comprises:

(i) subjecting the reaction product mixture containing an acetal or ketal together with water and unreacted aldehyde or ketone and alcohol to treatment with a solid base followed by, (ii) conducting pervaporation to remove water and methanol from the reaction product, wherein step (ii) comprises removing water from the reaction product mixture by bringing the reaction product mixture into contact with a first membrane having a flux density for water of 0.04 to 2.8 kg/(hm$^2$), and removing the methanol from the reaction product mixture by bringing the reaction product mixture into contact with a second membrane having a flux density for methanol of 2.0 to 100 kg/(hm$^2$), and wherein step (ii) is practiced under a temperature condition of about 60° C. to about 150° C. and under pressure conditions of a pressure on a retentate side of the membrane of up to 16 bar and a pressure on a permeate side of the membrane of about 1 to 500 mbar.

3. The process as in claim 1 or 2, which further comprises subjecting pervaporation retentate to treatment with an acid under conditions that favour acetalisation or ketalisation, followed by treating the pervaporation retentate with a base and removing the water and methanol from the reaction product by pervaporation.

4. The process as in claim 3, wherein the treatment of the pervaporation retentate is repeated until substantially pure acetal or ketal is obtained.

5. The process as in claim 1 or 2, wherein the solid acid is a strongly acidic polymer.

6. The process as in claim 5, wherein the strongly acidic polymer is a polystyrene sulfonic acid.

7. The process as in claim 2, wherein the solid base is a weakly basic ion exchange resin.

8. The process as in claim 1 or 2, which comprises preparing 2,2-dimethoxy propane from acetone and methanol.

9. The process as in claim 1 or 2, which further comprises heating the reaction product mixture during the pervaporation with heat produced in cooling the reaction product mixture for the acetalisation or ketalisation reaction.

* * * * *